United States Patent [19]

Mantese et al.

[11] Patent Number: 4,810,529
[45] Date of Patent: Mar. 7, 1989

[54] METHOD OF PRODUCING A MINIATURE INTERNAL REFERENCE GAS CHAMBER WITHIN AN AUTOMOTIVE, INTERNAL REFERENCE, SOLID ELECTROLYTE, LEAN OXYGEN SENSOR

[75] Inventors: Joseph V. Mantese, Troy; Adolph L. Micheli, Mt. Clemens; Jayant K. Bhagat, Troy; David B. Hicks, Farmington Hills, all of Mich.

[73] Assignee: General Motors Corporation, Detroit, Mich.

[21] Appl. No.: 135,578

[22] Filed: Dec. 21, 1987

Related U.S. Application Data

[63] Continuation of Ser. No. 904,419, Sep. 6, 1987, abandoned.

[51] Int. Cl.$^4$ .................. B05D 5/12; G01N 27/58
[52] U.S. Cl. .................. 427/123; 427/125; 427/126.2; 427/126.3; 427/126.4; 427/126.5; 204/412; 204/427; 204/429
[58] Field of Search .............. 204/421, 424–429; 264/41, 42–44, 48; 427/126.1, 126.2, 126.3, 126.4, 126.6, 123, 125, 372.2, 373, 227, 229, 383.3, 383.5, 383.7, 419.1, 419.2

[56] References Cited

U.S. PATENT DOCUMENTS

| | | | |
|---|---|---|---|
| 4,107,019 | 8/1978 | Takao et al. | 204/425 |
| 4,112,032 | 9/1978 | Blaszyk et al. | 264/42 |
| 4,244,898 | 1/1981 | Bandyopadhyay et al. | 264/43 |
| 4,563,432 | 1/1986 | Ehlert et al. | 264/42 |
| 4,588,540 | 5/1986 | Kiefer et al. | 264/43 |

*Primary Examiner*—John F. Niebling
*Assistant Examiner*—Ben C. Hsing
*Attorney, Agent, or Firm*—Domenica N. S. Hartman

[57] ABSTRACT

A method of producing a miniaturized, fixed volume, internal reference gas chamber comprising the pores of a porous material, suitable for use in a rapid response, highly precise, internal reference, solid electrolyte electrochemical-type oxygen sensor capable of detecting oxygen partial pressures in internal combustion engines operating within lean air/fuel mixtures is accomplished using a four step technique. A thin film layer of material is deposited onto a supporting substrate and patterned, said material comprises at least one component resistant to a subsequent removal step and at least one sacrificial component not resistant to the same subsequent removal step. The said material is then sealed everywhere except at an external orifice. The sacrificial component of said material is then decomposed and removed during a removal step, providing an interlocking network of porosity comprised within the porous component of said material. The internal reference gas chamber is positioned adjacent to the electrodes of the sense and pump cells comprised within the oxygen sensing device.

4 Claims, 1 Drawing Sheet

METHOD OF PRODUCING A MINIATURE INTERNAL REFERENCE GAS CHAMBER WITHIN AN AUTOMOTIVE, INTERNAL REFERENCE, SOLID ELECTROLYTE, LEAN OXYGEN SENSOR

This is a continuation of U.S. patent application Ser. No. 904,419, filed on Sept. 6, 1987 now abandoned.

The present invention generally relates to automotive exhaust gas sensors of the internal reference, solid electrolyte, electrochemical type. More particularly, this invention relates to a method of making a miniaturized internal reference gas chamber within a thin film oxygen sensor of this type suitable for high precision, quick response determinations of oxygen partial pressure ratios during lean internal combustion conditions.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the internal combustion control system of the automobile to provide accurate exhaust gas oxygen concentration measurements for determination of optimum combustion conditions, maximization of efficient fuel usage, and management of exhast emissions.

The conventional electrochemical type of oxygen sensor employed in automotive applications utilizes a thimble-shaped electrochemical galvanic cell to determine the relative amounts of oxygen present in the exhaust stream, as disclosed in U.S. Pat. No. 3,844,920 to Burgett et al. This type of oxygen sensor comprises an ionically conductive solid electrolyte material, typically zirconia stabilized by the addition of yttria, a porous electrode coating on the exterior contacting the exhaust or measuring gas, and a porous electrode coating on the interior contacting a known concentration of reference gas. The gas concentration gradient across the solid electrolyte produces a galvanic potential which is related to the differential of the partial pressures of the gas at the two electrodes.

Currently, these thimble-shaped, electrochemical-type oxygen sensors are employed in the exhaust gas system of an internal combustion engine to determine qualitatively whether the engine is operating at either of two conditions: (1) a fuel rich or (2) a fuel lean condition, as compared to stoichiometry. After equilibration, the exhaust gases from these two operating conditions have two widely different oxygen partial pressures. This information is provided to an air-to-fuel ratio control system, so that it can provide an average stoichiometric air-to-fuel ratio between the two conditions. However, due to the increasing demands for improved fuel utilization and emissions control, it is desirable to operate internal combustion engines exclusively within lean combustion conditions, i.e., air-to-fuel ratios between 15:1 and 25:1, where changes in the after-combustion oxygen partial pressures are only slight and gradual. The current oxygen sensor is not sensitive enough for this operating environment, since it merely provides the internal combustion control system with an ouput signal corresponding to the gross determination of either a rich or lean air-to-fuel ratio.

To be an effective component of the internal combustion control system operating exclusively within lean combustion conditions, the oxygen sensor must be extremely sensitive and capable of rapid, precise, absolute oxygen concentration measurements. It is desirable that the response time of the sensor be less than 0.1 second at a minimum temperature of 300° C. and a maximum oxygen concentration at the sensing electrode of about eight percent. The sensor must also be structurally durable to withstand the harsh automotive environment.

Internal reference oxygen sensors have been devised for lean engine operation and typically comprise two solid electrolyte galvanic cells; the first galvanic cell senses the gas to be measured, commonly referred to as the sense cell, while the second galvanic cell generates an accurately known internal gas reference, commonly referred to as the pump cell. The accurately known internal gas reference is generated by electrochemically pumping oxygen gas into and out of a hermetically sealed, fixed volume chamber by means of the pump cell. An external power source provides a potential across the solid electrolyte body of the pump cell. Electrons supplied at one electrode ionize gas molecules at the interface between that negatively biased electrode and the solid electrolyte. The gas ions are then transported through the solid electrolyte by ionic conduction. At the other electrode, the gas ions lose electrons and recombine into gas molecules. By reversing the polarity of the external circuit, oxygen gas can be transported in the other direction and subsequently pumped out of the fixed volume chamber. The partial pressure, i.e., concentration, of the oxygen gas in the gas mixture can be measured by simultaneoulsy sensing the oxygen partial pressure differential between the internal reference gas chamber and the gas mixture to be measured with the sense cell.

Internal reference, solid electrolyte oxygen sensors may be operated in various modes to determine gas concentration measurements. One method is to pump oxygen into the internal reference gas chamber with the pump cell until the voltage ouput at the sense cell equals some threshold value. The period of time required to pump that amount of oxygen into the chamber is related to the oxygen partial pressure in the exhaust gas. An alternative method is to maintain a constant oxygen pressure in the internal reference gas chamber and determine exhaust oxygen concentration from the voltage output measurements at the sense cell.

If one elects to cycle oxygen out of and back into the reference gas chamber each time one chooses to measure oxygen partial pressure in a gas mixture, sensor response time will be proportional to the volume of the internal reference gas chamber, i.e., the number of gas molecules pumped into and out of the chamber. Therefore, it is desirable to provide a chamber of minimum volume so that the sensor response time is minimized. A prior improved oxygen sensor disclosed in "Automotive, Internal Reference, Solid Electrolyte, Lean Oxygen Sensor", now U.S. Pat. No. 4,668,374 laterally positions both the sense and pump cell components on a single substrate and uses conventional thin film deposition techniques with a thick film capping layer to produce an internal reference gas chamber of minimal volume. Our invention further improves and miniaturizes the internal reference gas chamber by disclosing a method of making an internal reference gas chamber comprised of the pores of a porous material that spaces adjacent electrodes of the pump and sense cells. The volume of the internal reference gas chamber and amount of oxygen pumped into and out of the chamber during one pump cycle of the oxygen sensor are further reduced, maximizing the efficiency of the oxygen sensor.

SUMMARY OF THE INVENTION

It is an object of our invention to provide a method of making a miniature internal reference gas chamber between electrodes for use in an internal reference, solid electrolyte, oxygen sensor suitable for use in internal combustion engines operating with lean air-to-fuel ratios. It is a further object of our invention that the miniature internal reference gas chamber be provided by the pores of a porous thin film material spacing pump and sense cell electrodes in the sensor.

In accordance with a preferred embodiment of our invention, these and other objects and advantages are accomplished as follows.

This invention comprehends a method of making a miniature internal reference gas chamber for use in a thin film, internal reference, solid electrolyte oxygen sensor comprising mutually and laterally disposed galvanic sense and pump cells on a non-ionically conductive substrate. The internal reference gas chamber, hereinafter referred to as the chamber, comprises the pores of a thin film layer of porous material and is made by the following four-step technique.

Using conventional thin film deposition techniques, a layer of material is deposited onto a planar surface comprised within the oxygen sensing device. The thin film material, referred to as the bi-component material, comprises at least two components, one component which is resistant to a subsequent chemical or thermal removal step and at least one component which is not resistant to the same subsequent chemical or thermal removal step. The separate components within the bi-component material may comprise two distinct materials co-deposited together, such as a metal and its oxide, a metal and a ceramic, two different ceramics, or a ceramic and inorganic material. The bi-component material may also comprise different crystalline phases of the same material. Although the preferred embodiments of our invention disclose the use of materials comprising only two components to form the internal reference gas chamber, other suitable materials comprising more than two components may also be used.

The bi-component material is patterned using conventional thin film patterning techniques and non-selective etchants to form at least two distinct configurations within the oxygen sensor. The first patterned configuration delineates the volume of material which will provide the pores comprising the internal reference gas chamber after the subsequent removal step. This first configuration of material contacts the first porous platinum electrode of the sense cell and the first porous platinum electrode of the pump cell. The second patterned configuration delineates a serpentine, tortuous channel connecting the first configuration of material to an external orifice. At least one layer of a thin film material is deposited on top of the first and second configurations of bi-component material so that the bi-component material is totally sealed except at the external orifice provided on the supporting substrate.

The final step involves selectively removing, chemically or thermally, at least one component of the bi-component material from both patterned configurations of material via the serpentine tortuous path and external orifice so that at least one component of the multi-component material remains. The pores formed by the removed component from the first patterned configuration comprise the interal reference gas chamber. Porosity due to the removed component in the second patterned configuration, the serpentine tortuous channel, results in a negligible oxygen leak rate into the chamber at the preferred oxygen pump rates, due to the design of the serpentine tortuous channel.

This invention produces a miniaturized, fixed volume, internal reference gas chamber for use in an oxygen sensing device suitable for detecting oxygen concentration measurements in lean combustion conditions. The internal reference gas chamber comprises the porosity included within a porous material. A smaller amount of oxygen molecules are required to be pumped into and out of the internal reference gas chamber during sensor operation with this oxygen sensing device than with conventional internal reference, solid electrolyte oxygen sensors, therefore improving sensor response time and efficiency.

Other objects and advantages of our invention will be better appreciated from the following detailed description.

DETAILED DESCRIPTION OF THE INVENTION

Internal reference, solid electrolyte oxygen sensing devices suitable for detecting oxygen partial pressures during lean combustion conditions and comprising an internal reference gas chamber and two galvanic cells, a sense cell and a pump cell, have been disclosed in U.S. Ser. No. 882,689 filed July 7, 1986 entitled "Gas Sensor and Method of Fabricating Same" and U.S. Pat. No. 4,668,374 entitled "Automotive, Internal Reference, Solid Electrolyte, Lean Oxygen Sensor", both of which applications are assigned to the assignee of this invention. Our invention involves forming a distinctive new type of internal reference gas chamber within such an internal reference, solid electrolyte oxygen sensing device.

Figure 1:
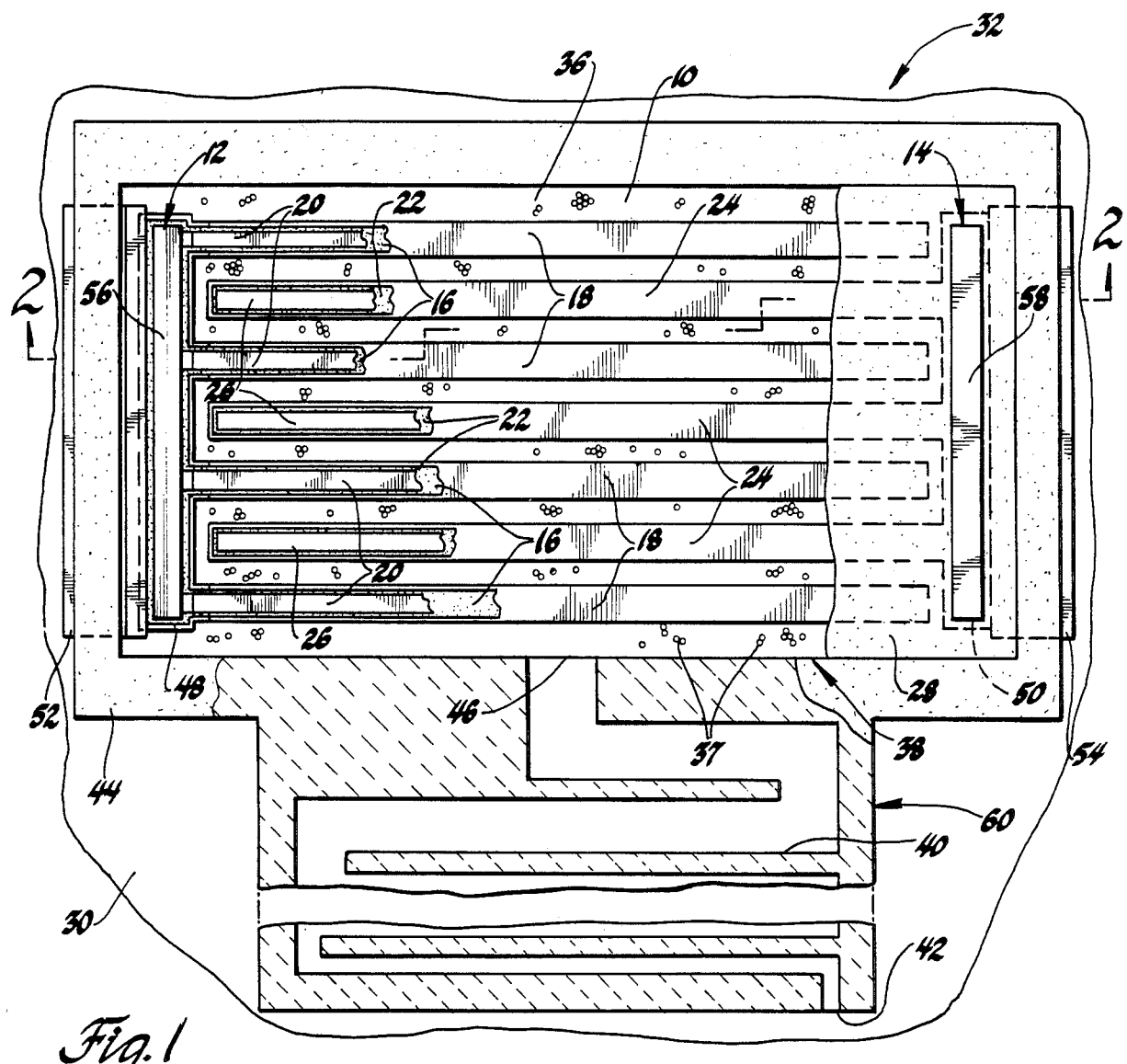
FIG. 1 is a plan view of an oxygen sensing device comprising an internal reference gas chamber and serpentine tortuous path made in accordance with a preferred embodiment of this invention.
Figure 2:
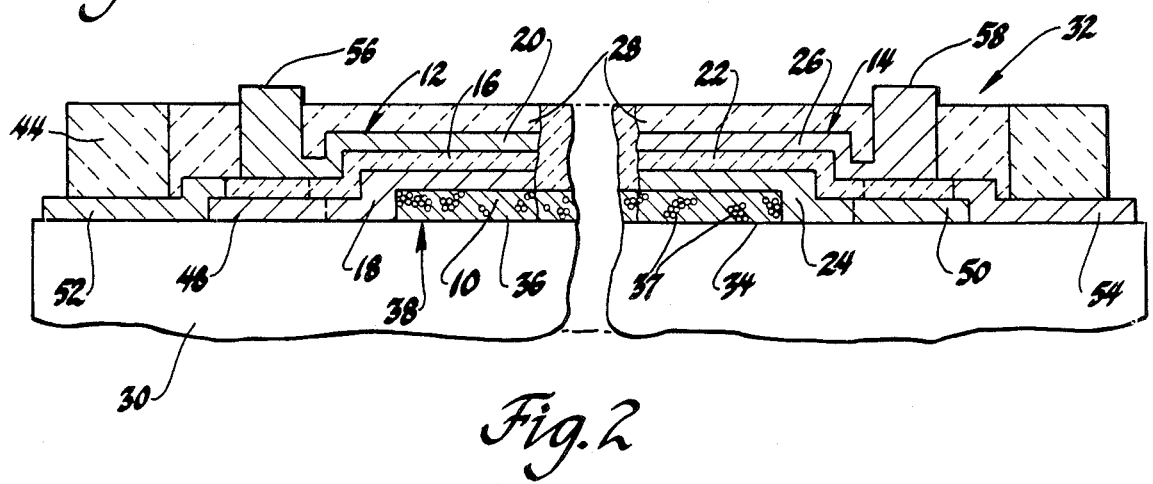
FIG. 2 is a cross-sectional view along the line 2—2 of the oxygen sensing device shown in FIG. 1 wherein the pump and sense cell components overlay the internal reference gas chamber.

In our invention, the internal reference gas chamber 10, also referred to as the chamber, is provided by the pores 37 of a porous material 36, as shown in FIGS. 1 and 2. The elements overlaying the internal reference gas chamber 10 in FIG. 2 are the conventional sense and pump cell components such as found within prior internal reference, solid electrolyte oxygen sensors, and comprised of the conventional materials. For example, the galvanic sense cell 12 comprises an yttria stabilized zirconia thin film solid electrolyte 16 and two porous platinum electrodes 18 and 20, the first electrode 18 arranged for contact with the internal reference gas chamber 10 and the second electrode 20 arranged for contact with an external gas to be measured. The galvanic pump cell 14 comprises an yttria stabilized zirconia thin film solid electrolyte 22 and two porous platinum electrodes 24 and 26; the first electrode 24 contacts the internal reference gas chamber 10. An electrically insulating layer of material 28 is provided at least in the region between the sense and pump cell components, 12 and 14 respectively.

A highly polished silicon substrate 30, about 3.0 inches in diameter and about 0.015 inch thick, is the preferred supporting member for our oxygen sensing device 32 and internal reference gas chamber 10. However, this invention is not limited to the use of silicon as the substrate material nor to the use of a substrate of that size. Using conventional thin film deposition techniques, a thin film layer of material 34, which will subsequently provide the pores comprising the internal reference gas chamber, is deposited onto the planar surface of the silicon substrate.

This thin film layer of material 34, referred to as the bi-component material, comprises at least two distinct components, at least one component which is resistant to the subsequent chemical or thermal removal step required to produce the pores comprising the internal reference gas chamber 10 and at least one component which is not resistant to the subsequent chemical or thermal removal step. Hereinafter, the chemical or thermal removal step will be referred to as the removal step. The thin film layer of material 34 is referred to as the bi-component material although it is not restricted to comprising only two components. The distinct components of the bi-component material 34 may comprise actual distinct materials co-deposited together, such as a metal and ceramic, two different ceramics, or a ceramic and organic material. The distinct components may comprise different phases or crystal structures of the same material. The component which is decomposed and removed during the removal step provides the volume of pores 37 which comprise the internal reference gas chamber 10 and is hereinafter referred to as the sacrificial component. The component which resists the removal step and provides the support for the pore structure and chamber is hereinafter referred to as the porous component 36. An etchant that will attack one of the components significantly more than the other is referred to as a selective etchant.

Using conventional thin film deposition and patterning techniques, a blanket thin film of the bi-component material 34 is deposited onto the surface of the silicon substrate 30. The blanket thin film 34 is patterned to form a configuration having at least two distinct but contiguous, i.e., integral, parts, using means that will remove both components of the film simultaneously, such as a non-selective etchant like hydrofluoric acid, or means such as a mechanical mask during deposition that will prevent deposition of the bi-component material on the silicon substrate in selected regions. The first integral part 38 of the configuration of bi-component material 34 delineates an area, about 300 microns wide by about 200 microns long, and will subsequently comprise the internal reference gas chamber 10 and porous support material 36. This first part of the configuration 38 is also referred to as the first region. The first platinum electrode 18 of the galvanic sense cell 12 and the first platinum electrode 24 of the galvanic pump cell 14 will contact the top surface of this first region 38.

The second integral part 60 of the configuration of bi-component material 34 is patterned at the same time as the first part to form a serpentine, tortuous channel 40, referred to as the channel. The channel 40 extends from the first integral part 38 onto about a 200 micron square area of the silicon substrate adjacent to and on the same planar surface as the first integral part 38. This second patterned configuration 60 of bi-component material 34 is also referred to as the second region. The opposite end of the channel 40 from the first region 38 will provide an external orifice 42 in combination with a hermetic film 44 subsequently deposited on the silicon substrate 30. The thin film layer 34 of bi-component material delineating the channel 40 is about 40 microns wide at the interface 46 of the first and second patterned configurations 38 and 60, respectively, and narrows gradually to about 10 microns at the external orifice 42 end. The channel 40 is about 1000 microns in length with about four to six 180 degree turns along its length.

The bi-component material 34 is deposited to a thickness of at least about 0.1 micron and no greater than about 1.0 micron. A minimum thickness is desired so that the fixed volume chamber 10 is miniaturized, resulting in a quick sensor response time, and so that the oxygen leak rate into the chamber is negligible in comparison to the oxygen pump rate into and out of the chamber. However, there must be sufficient thickness to insure continuous surface coverage on the substrate by the material and to insure adequate volume to allow complete removal of the sacrificial component during the removal step. The preferred thickness of the deposited thin film bi-component layer 34 is about 0.3 micron; however, no significant detrimental effects have been observed when the thickness of the bi-component layer 34 ranges between about 0.1 micron and about 20.0 microns.

Using conventional thin film deposition and patterning techniques, the galvanic sense cell 12 and galvanic pump cell 14 are deposited on top of the bi-component material 34 in the first region 38 of the oxygen sensor 32. A porous platinum film is blanket deposited on top of and over the sides of the bi-component material 34 in the first region 38, covering an area about 250 microns square. The porous platinum film is patterned using conventional techniques to form the first electrode 18 of the sense cell 12 and the first electrode 24 of the pump cell 14, although no detrimental effects have been observed when this platinum film is not patterned and therefore forms a common first electrode for both the sense cell and pump cell. Both electrodes 18 and 24 are interdigitated with respect to each other as shown in FIG. 1 and both electrodes 18 and 24 contact the internal reference gas chamber 10 that will subsequently be formed in this region 38. Each electrode, 18 and 24 respectively, comprises a main stem 48 and 50, about 10 microns wide by about 150 microns long, and about three or four evenly spaced perpendicular extensions from the main stem, each about 10 microns wide by about 240 microns long. The interdigitated electrode patterns cover about 80 percent of the available surface area within the first region. The thickness of the porous platinum electrode layer 18 and 24 may range between about 0.1 micron and 1.0 micron with a preferred thickness being about 0.3 micron to insure adequate coverage and minimize sensor response time.

The thin film solid electrolyte layer, preferably zirconia partially or fully stabilized in its cubic form by additions of about 4–8 mole percent yttria, is blanket deposited and then patterned using conventional techniques, to form a discrete patch of sense cell solid electrolyte material 16 on the top surface of the first porous platinum electrode 18 of the sense cell 12. Concurrently, it is patterned to form a discrete patch of pump cell solid electrolyte 22 on the top surface of the first porous platinum electrode 24 of the pump cell 14. The patches of solid electrolyte film 16 and 22 are each patterned to cover almost completely, about 95 percent (not to scale on drawings), and thus have substantially the same configuration as the top surface of its respective underlying interdigitated porous platinum electrode 18 and 24. The thickness of the yttria-stabilized zirconia solid electrolyte film may range between about 0.1 and about 1.0 micron with the preferred thickness again being about 0.3 micron.

A second porous platinum thin film blanket layer is deposited and patterned, using conventional techniques, into electrodes 20 and 26 on the top surface of each solid electrolyte layer 16 and 22 patch. This forms the second electrode 20 of the sense cell 12 and the second electrode 26 of the pump cell 14. Each second porous platinum electrode 20 and 26 is patterned to cover about 60 percent of the top surface of the solid electrolyte patch 16 and 22 beneath it with the same general configuration but wholly within the boundary of the solid electrolyte patch, as shown in FIG. 1. The thickness of the thin film second porous platinum electrode layers 20 and 26 may range between about 0.1 micron and about 1.0 micron, with the preferred thickness again being about 0.3 micron.

A blanket thin film of non-porous and electrically conductive material is then deposited onto the surface of the foregoing device. It is patterned using conventional techniques to form two bands 52 and 54, each about 50 microns wide and about 175 microns long. The first band 52 of non-porous electrically conductive material overlaps a portion of the main stem 48 of the first porous platinum electrode 18 of the sense cell 12. The second band 54 of non-porous electrically conductive material overlaps a portion of the main stem 50 of the first porous platinum electrode 24 of the pump cell 14. These bands 52 and 54 of non-porous electrically conductive material provide the electrical leads for connection to external electrical measuring equipment (not shown) and prevent oxygen leakage out of the internal reference gas chamber 10 through the first porous platinum electrodes 18 and 24.

A blanket thin film 28 of non-porous and electrically insulating material is then deposited onto the surface of the foregoing product. It is patterned using conventional techniques to expose (a) the interior portions of the upper surface of the main stem 56 and 58 of each second electrode 20 and 26, (b) the opposite end of the channel from the first integral region 38 so to provide the external orifice 42, and (c) the thin film bands 52 and 54 of non-porous electrically conductive material overlapping the first electrodes 18 and 24 of the sense and pump cells 12 and 14. It should be mentioned that the otherwise exposed surface area of the bi-component material layer 34 between the interdigitated sense and pump cell 12 and 14 components in the first region 38 is thus covered. The insulating layer 28 concurrently deposited onto the entire surface area of the second region 60 comprising the serpentine, tortuous channel 40 is patterned to form a patch about 200 microns square. Therefore, the entire layer of bi-component material 34 is sealed by the insulating layer 28 except at the external orifice 42. The thickness of the insulating layer 28 may vary between about 0.3 micron and about 3.0 microns, depending on the thickness of the thin film layers comprised within the galvanic sense and pump cells 12 and 14. As a practical matter, for good step coverage the preferred thickness of the insulating layer is about 0.9 micron, at least in the region between the interdigitated sense and pump cell components 12 and 14. The preferred material for the insulating layer is silicon nitride ($Si_xN_y$); however, other suitable oxygen impermeable and electrically insulative materials may be used.

Means are provided (not shown) so that the second porous platinum electrode 20 of the sense cell 12 contacts an external gas to be measured, i.e., the internal combustion engine exhaust gases, and so that the second porous platinum electrode 26 of the pump cell 14 contacts an ambient oxygen gas partial pressure, i.e., ambient air or the exhaust gas. Means are also provided (not shown) so that the second electrodes 20 and 26 of the sense and pump cells 12 and 14 are connected to electrical measuring equipment. Any acceptable means to achieve these results can be used, as they form no part of this invention.

Although our invention discloses an oxygen sensing device 32 comprising galvanic sense and pump cells 12 and 14 overlaying the internal reference gas chamber 10, our invention is not limited to this configuration. It is foreseeable that a suitable embodiment using our invention comprises the internal reference gas chamber 10 overlaying the galvanic sense and pump cell components 12 and 14.

Our invention embraces three distinct materials as the porous component 36 of the bi-component material 34: (1) a porous alumina ceramic, commonly referred to as aluminum oxide or $Al_2O_3$, (2) a porous silica glass, commonly referred to as $SiO_2$, and (3) a porous platinum metal. The porous component resists the removal step and provides the support for the chamber pore structure. In order to insure adequate porosity and volume of the internal reference gas chamber 10 for (1) successful operation of our oxygen sensing device 32, (2) for thorough removal of the sacrificial component, and (3) for structural integrity of the internal reference gas chamber 10 after the removal step, the porous component 36 should comprise not greater than about 55 percent and not less than about 25 percent of the total volume of the bi-component layer 34.

The removal step comprises chemically or thermaly decomposing and removing the sacrificial component of the bi-component layer 34. The sacrificial component is removed from the first and second regions 38 and 60 of the oxygen sensing device 32 via the serpentine tortuous channel 40 and external orifice 42. After removal of the sacrificial component, the vacant pores 37 provided by the sacrificial component provide an interlocking network of porosity within the porous material 36. This interlocking network of porosity 37 comprises the internal reference gas chamber 10 suitable for use in a fast response, highly precise, oxygen partial pressure sensing device. The volume of the internal reference gas chamber 10 comprised by the porosity 37 of the porous component 36 should not exceed about 20,000 microns$^3$.

A first embodiment of our invention discloses an alumina ceramic porous component 36 in the bi-component material layer 34 to provide the porosity 37 comprising the internal reference gas chamber 10. The alumina is co-deposited with a metal using conventional techniques, such as titanium, to the desired thickness, preferably about 0.3 micron, and patterned to form the first and second regions 38 and 60 of the bi-component layer 34. After at least one thin film layer of material comprised within a component of the oxygen sensor 32 has been deposited on top of the first and second regions 38 and 60 of the bi-component layer 34, the titanium is selectively removed from the first region 38 and second region 60 of the bi-component layer 34 through the serpentine tortuous channel 40 and external orifice 42 provided on the silicon substrate 30. The removal step comprises immersing the oxygen sensor in a solution of about three parts hydrofluoric acid (49 weight percent), about one part hydrogen peroxide (30 weight percent), about 10 parts isopropyl alcohol, and about 20 parts water. At room temperature, the removal rate is about 1500 angstroms of thickness per minute. The alumina ceramic, as well as the other components of the sensor, resists the acid etch and forms the structural support 36 for the porosity 37 comprising the internal reference gas chamber 10.

The alumina ceramic may also be co-deposited with an organic film, such as commercially available PD-08 Colloidal Alumina Desicant, using conventional techniques, to the desired thickness and pattern. After at least one thin film layer of material comprised within a component of the oxygen sensor 32 has been deposited over the first and second regions 38 and 60 of the bi-component layer 34, the organic film is thermally removed. The thermal removal step comprises heating the oxygen sensor to about 500° C. for about 10 minutes. The organic film is removed from the first and second regions 38 and 60 of the bi-component layer 34 through the serpentine tortuous channel 40 and external orifice 42 provided on the silicon substrate 30. This thermal removal step causes no adverse effects to the the alumina or other material components comprised within the oxygen sensor 32. Therefore, an internal reference gas chamber 10 is provided by the interconnecting porosity 37 comprised within the alumina ceramic.

A second preferred embodiment of our invention uses silica glass as the porous component 36 comprised within the thin film, bi-component layer 34. The silica glass is co-deposited using conventional techniques, with $Na_2O_24(B_2O_3)$ to the preferred thickness, about 0.3 micron, and patterned to form the first and second regions 38 and 60 of the bi-component layer 34. After at least one other thin film layer of material comprised within the oxygen sensor 32 is deposited onto the first and second regions 38 and 60 of the bi-component layer 34, the $Na_2O_24(B_2O_3)$ is selectively removed by immersing the device in an approximately 50 percent nitric acid in water solution, at about 150° C. for about 24 hours. The $Na_2O_24(B_2O_3)$ is selectively removed through the serpentine tortuous channel 40 and external orifice 42 provided on the silicon substrate 30. The resulting porous silica glass provides the support 36 for the porosity 37 comprising the internal reference gas chamber 10.

Another method of obtaining our second preferred embodiment involves co-depositing the silica glass with an organic film to the desired thickness and pattern, and subsequently thermally removing the organic film. This process is identical to the process disclosed in our first embodiment using alumina ceramic and an organic film, resulting in an interlocking network of pores 37 supported by the silica glass.

Our invention also embraces an internal reference gas chamber 10 comprising the porosity within a porous platinum metal film. The platinum metal is co-deposited with titanium metal to the desired thickness, about 0.3 micron, and patterned to form the first and second regions 38 and 60 of the oxygen sensor 32. The platinum and titanium metals do not bond together. After at least one layer of material comprising a component of the oxygen sensor 32 is deposited on top of the first and second regions 38 and 60 of the bi-component layer 34, the titanium metal is selectively etched away with a solution of about three parts hydrofluoric acid (49 weight percent), about one part hydrogen peroxide (30 weight percent), about 10 parts isopropyl alcohol, and about 20 parts water. At room temperature, the removal rate is about 1500 angstroms of thickness per minute. The platinum resists the acid treatment, providing the structural support 36 for the interlocking network of pores 37 comprising the internal reference gas chamber 10.

A thin film porous platinum metal support layer 36 comprising the internal reference gas chamber 10 is also obtained by the following methods. The platinum metal is co-deposited with an inorganic material, such as silicon dioxide or silicon nitride, to the desired configuration. After at least one other layer of material comprised within the oxygen sensor 32 is deposited on top of the bi-component layer 34, the inorganic is removed using a fluorine plasma etch, providing an internal reference gas chamber 10 supported by the porous platinum metal. An alternative method, disclosed in our first and second embodiments comprising porous alumina ceramic and porous silica glass, co-deposits platinum metal with an organic film, and subsequently thermally removes the organic film.

A miniaturized internal reference gas chamber 10 provided by the porosity 37 of a porous material 36 suitable for use in a rapid response, highly precise oxygen sensing device 32 for detecting air/fuel ratios for internal combustion engines operating within lean air/fuel mixtures is provided by any of our disclosed embodiments. Various modifications of our invention which basically rely on the teachings disclosed in our invention, such as depositing an inherently porous material for the porous component without a sacrificial component or selectively removing the sacrificial component prior to depositing all of the thin film layers, are properly considered within the scope of this invention.

The embodiments of the invention in which an exclusive property or privilege is claimed are defined as follows:

1. A method of producing an internal reference gas chamber in a thin film, internal reference, solid electrolyte oxygen sensor having laterally disposed galvanic sense and pump cells comprising the steps of:
   (a) providing a non-ionically conductive substrate;
   (b) depositing a first this film layer of material onto a planar surface of said substrate within the oxygen sensor, said material comprising not less than two distinct components, a sacrificial component and a porous component, to a thickness of not less that about 0.1 micron and not greater than about 20.0 microns;
   (c) patterning said thin film layer of material to form at least two distinct patterned configurations, the first patterned configuration of said material contacts an electrode comprised within the galvanic sense cell and an electrode comprised within the galvanic pump cell, the second patterned configuration of said material delineates a serpentine, tortuous channel connecting the first patterned configuration of said material to an external orifice;
   (d) depositing a second thin film layer of material onto said patterned first layer of material so that said patterned first layer of material is enveloped everywhere except at said external orifice; and (e) subsequently selectively removing said sacrificial component of said material via said serpentine, tortuous channel and said external orifice by thermal or chemical decomposition, so that at least one component, the porous component, of said material remains;

effective to produce a miniaturized internal reference gas chamber provided by the porosity of a porous material for use in a rapid response, highly precise oxygen partial pressure detector for detecting air/fuel ratios for internal combustion engines operating with lean air/fuel mixtures.

2. The method of claim 1 wherein the porous material remaining after selectively removing the sacrificial component from the said material is a porous alumina ceramic.

3. The method of claim 1 wherein the porous material remaining after selectively removing the sacrificial component of the said material is a porous silica glass.

4. The method of claim 1 wherein the porous material remaining after selectively removing the sacrificial component from the said material is a porous platinum metal.

* * * * *